United States Patent
Metzinger et al.

(10) Patent No.: US 8,632,543 B2
(45) Date of Patent: Jan. 21, 2014

(54) COMPOSITE INTRAMEDULLARY NAIL (75) Inventors: Anthony Metzinger, Winona Lake, IN (US); Stuart Grant, Warsaw, IN (US); Jason Yambor, Fort Wayne, IN (US)

(73) Assignee: Biomet C.V., Gibraltar (GI)

(*) Notice: Subject to any disclaimer, the term of this patent is extended or adjusted under 35 U.S.C. 154(b) by 1125 days.

(21) Appl. No.: 11/904,844

(22) Filed: Sep. 28, 2007

(65) Prior Publication Data
US 2009/0088752 A1 Apr. 2, 2009

(51) Int. Cl.
*A61B 17/58* (2006.01)

(52) U.S. Cl.
USPC .......................................................... 606/62

(58) Field of Classification Search
USPC ............................................ 606/62–68, 304
See application file for complete search history.

(56) References Cited

U.S. PATENT DOCUMENTS

| | | | | | |
|---|---|---|---|---|---|
| 4,457,301 | A | * | 7/1984 | Walker | 606/62 |
| 4,495,664 | A | * | 1/1985 | Blanquaert | 623/23.36 |
| 5,053,035 | A | | 10/1991 | McLaren | |
| 5,429,640 | A | * | 7/1995 | Shuler et al. | 606/64 |
| 5,433,718 | A | * | 7/1995 | Brinker | 606/62 |
| 5,935,127 | A | | 8/1999 | Border | |
| 6,077,265 | A | * | 6/2000 | Werding et al. | 606/67 |
| 6,120,504 | A | | 9/2000 | Brumback et al. | |
| 6,387,098 | B1 | * | 5/2002 | Cole et al. | 606/62 |
| 6,551,321 | B1 | | 4/2003 | Burkinshaw et al. | |
| 6,709,436 | B1 | | 3/2004 | Sturgeon et al. | |
| 6,783,529 | B2 | | 8/2004 | Hover et al. | |
| 6,786,908 | B2 | | 9/2004 | Hover et al. | |
| 7,604,653 | B2 | * | 10/2009 | Kitchen | 606/257 |
| 2002/0111629 | A1 | * | 8/2002 | Phillips | 606/62 |
| 2003/0069581 | A1 | * | 4/2003 | Stinson et al. | 606/62 |
| 2003/0195515 | A1 | | 10/2003 | Sohngen | |
| 2005/0187555 | A1 | * | 8/2005 | Biedermann et al. | 606/72 |
| 2005/0216007 | A1 | * | 9/2005 | Woll et al. | 606/62 |
| 2007/0173834 | A1 | * | 7/2007 | Thakkar | 606/62 |

FOREIGN PATENT DOCUMENTS

| | | |
|---|---|---|
| WO | WO 97/03611 | 2/1997 |
| WO | 0061018 | 10/2000 |
| WO | 2005009258 | 2/2005 |

(Continued)

OTHER PUBLICATIONS definition for "match", www.thefreedictionary.com, accessed Aug. 20, 2012.*

(Continued)

*Primary Examiner* — Jan Christopher Merene
(74) *Attorney, Agent, or Firm* — Harness, Dickey (57) ABSTRACT

An intramedullary nail for use in a medullary canal of an epiphysis and a diaphysis of a long bone is provided. The nail includes a body having a length in a longitudinal direction and a width in the transverse direction normal to the longitudinal direction. The body has a diaphyseal portion and a first epiphyseal portion. The diaphyseal portion has an external periphery configured for placement in the medullary canal of the diaphysis of the long bone. The diaphyseal portion defines a longitudinally extending first surface of the diaphyseal portion. The first surface defines a longitudinally extending first void. The first epiphyseal portion extends from the diaphyseal portion. The first epiphyseal portion is configured for placement in the medullary canal of the first epiphysis of the long bone. The nail also includes a first insert positioned in the longitudinally extending first void of the diaphyseal portion. The first insert and the diaphyseal portion of the body are made from different materials.

23 Claims, 9 Drawing Sheets

(56) References Cited

FOREIGN PATENT DOCUMENTS

| | | |
|---|---|---|
| WO | WO 2005/053551 | 6/2005 |
| WO | WO 2005/094706 | 10/2005 |
| WO | WO 2005/096976 | 10/2005 |
| WO | WO 2006/041460 | 4/2006 |

OTHER PUBLICATIONS

Patent Cooperation Treaty, International Search Report in a corresponding PCT application (i.e. PCT/US2008/076951), dated Feb. 10, 2009, 6 pages.

* cited by examiner

COMPOSITE INTRAMEDULLARY NAIL

TECHNICAL FIELD

The present invention relates generally to the field of orthopaedic trauma, and more particularly to a device for positioning in the medullary canal of a long bone.

BACKGROUND

The skeletal system includes many long bones that extend from the human torso. These long bones include the femur, fibula, tibia, humerus, radius and ulna. These long bones are particularly exposed to trauma from accidents, and, as such, may be fractured during a trauma. Automobile accidents, for instance, are a common cause of trauma to long bones. In particular, the femur and tibia frequently fracture when the area around the knee is subjected to a frontal automobile accident.

Often the distal end or proximal portions of the long bone, for example the femur and the tibia, are fractured into several components and must be realigned. Mechanical devices, commonly in the forms of pins, plates, screws, nails, wires and external devices are commonly used to attach fractured long bones. The pins, plates, wires, nails and screws are typically made of a durable material compatible to the human body, for example titanium, stainless steel or cobalt chromium.

Subtrochanteric and femoral shaft fractures have been treated with the help of intramedullary rods or nails, which are inserted into the marrow canal of the femur to immobilize the femur parts involved in fractures.

Figure 9:
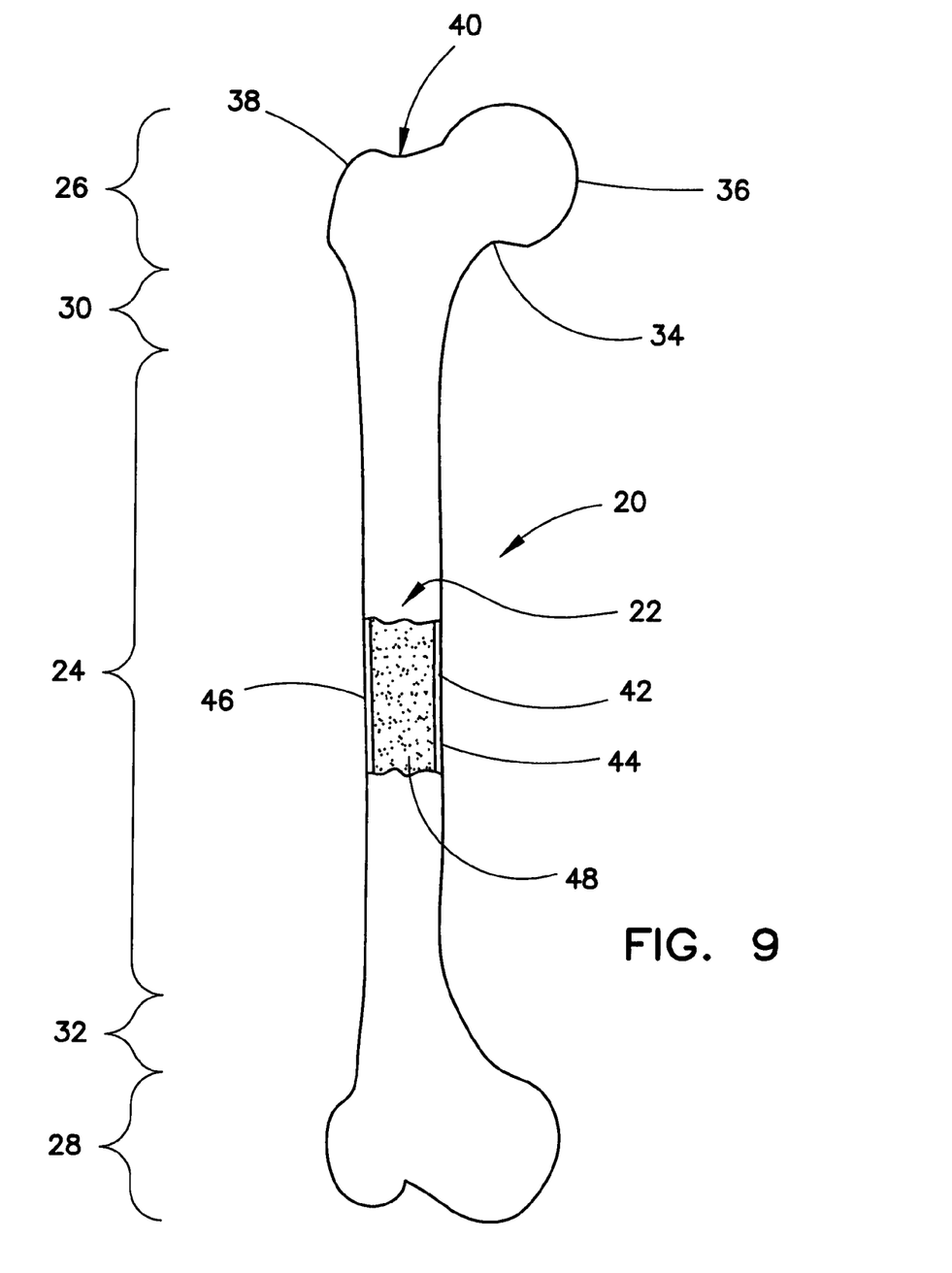
FIG. 9 is a perspective view of a human femur.

As shown in FIG. 9, a long bone 20 is shown in the form of a femur. The femur 20 is typical of long bones and includes a central shaft portion known as a diaphysis 24 as well as opposed portions extending from the diaphysis 24. The opposed portions include a proximal end portion know as a proximal epiphysis 26 and a distal end portion where know as a distal epiphysis 28. The femur 20 further includes a transition zone know as a proximal metaphysis 30 positioned between the diaphysis 24 and the proximal epiphysis 26. A transition zone know as a distal metaphysis 32 is positioned between the diaphysis 24 and the distal epiphysis 28. The proximal epiphysis 26 includes a neck 34 from which a head 36 extends. A hump on the outer periphery of the proximal epiphysis 26 to which tissue is attached is known as a greater trochanter 38 and is opposed to the head 36 and neck 34. A central recess in the end of the distal epiphysis 28 is known as a piriformis fossa 40. The femur 20 includes a harder outer layer of bone called cortical bone 42. The cortical bone 42 defines a first external cortical wall 44 and an opposed second external cortical wall 46. Softer cancellous bone 48 is found in bone canal 22, interior of the cortical bone 42.

Figure 10:
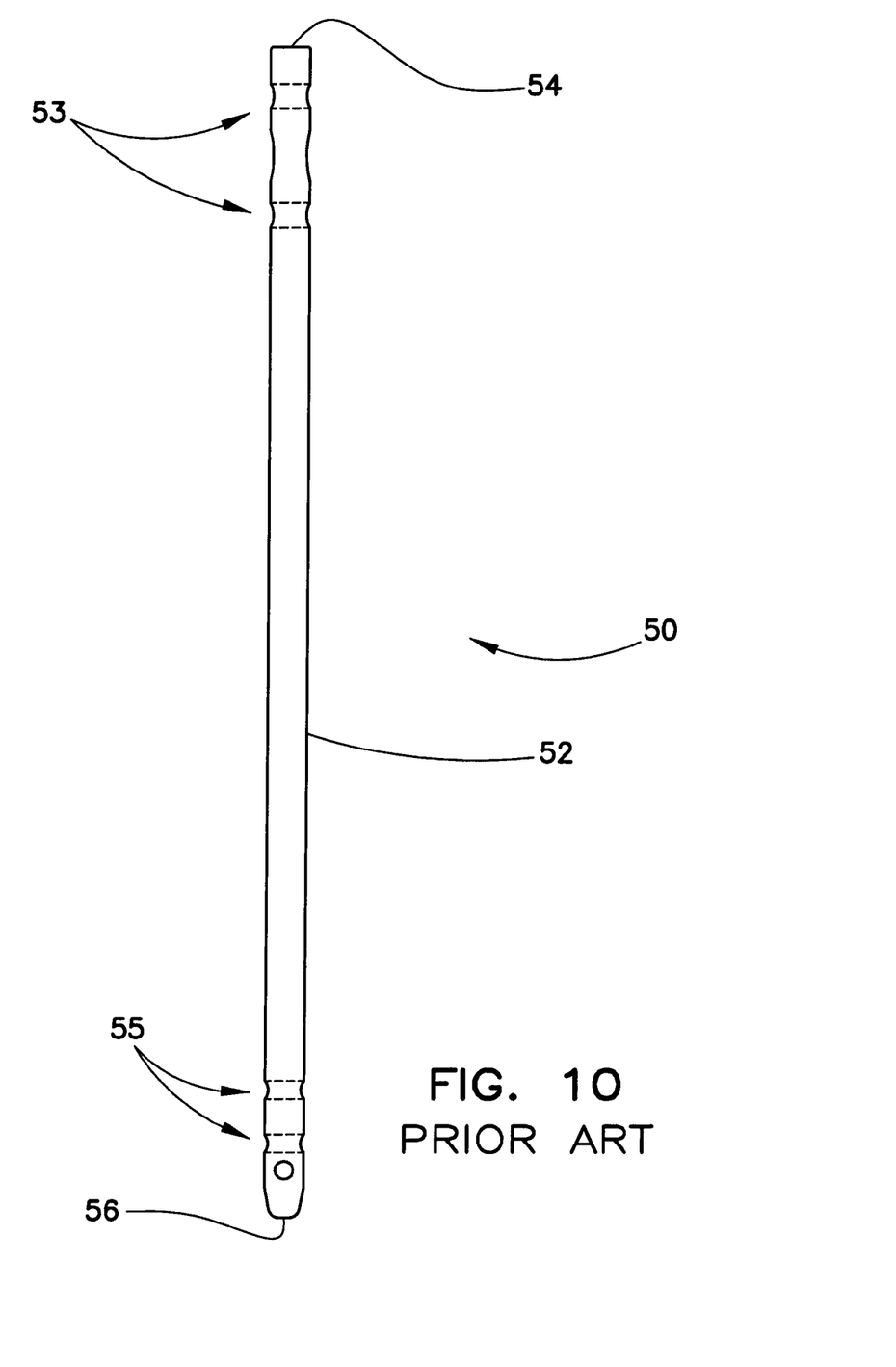
FIG. 10 is an anterior/posterior view of a prior art intramedullary nail.

Referring now to FIG. 10 a prior art intramedullary nail 50 is shown. The intramedullary nail 50 includes a cylindrical body 52. A first set of transverse openings 53 are positioned near proximal or first end 54 of the intramedullary nail 50 and a second set of transverse openings 55 are positioned near distal or second end 56 of the intramedullary nail 50. A single angled cross-nail or locking screw (not shown) is inserted through the femur into the first set of transverse openings 53 in the proximal end 54 of the intramedullary nail 50 to secure the nail 50 axially in the bone canal. In some varieties, one or two screws may also be inserted through the femoral shaft and through the second set of transverse openings 55 in the distal end 56 of the intramedullary nail 50. The prior art intramedullary nail 50 has been successfully employed in treating fractures in femurs.

Intramedullary nails typically have a generally cylindrical cross section and may be cannulated. The intramedullary canals of long bones of humans such as femurs have a shape that varies from person to person. The intramedullary canals of femurs have an arc or bow in the anterior posterior plane. Intramedullary nails, such as femoral nails, are available with a bowed shape based on anatomical statistics to account for the bow of the human intramedullary canal. Femoral nails are typically inserted in the bone through the proximal epiphysis of the long bone, with the entry point positioned either centrally, through the piriformis fossa, or on a side, through the greater trochanter. Femoral nails are typically either in the form of a piriformis fossa nail, with a generally linear proximal end portion for insertion through the piriformis fossa, or in the form of a greater trochanter nail, with a generally curved proximal end portion for insertion through the greater trochanter. The linear proximal end portions and the curved proximal end portions that are shaped to account for the insertion of the nail in the piriformis fossa and the greater trochanter, respectively, compromise the otherwise anatomical shape of the nail when fully inserted and often result in an improper fit. As a result, in spite of efforts to provide an anatomical intramedullary nail, anatomical differences from patient to patient result in nails often failing to fit properly in the canal. If a nail does not match the human bone canal, the nail may impart thigh pain while the implant is in the human bone canal. Further, each of these two separate nail configurations needs to be manufactured and made available for surgeries. Therefore, it would be advantageous to provide a nail that could be easily modified to fit the patient.

SUMMARY

According to one embodiment of the present disclosure, there is provided an intramedullary nail for use in a medullary canal of an epiphysis and a diaphysis of a long bone. The nail includes a body having a length in a longitudinal direction and a width in the transverse direction normal to the longitudinal direction. The body has a diaphyseal portion and a first epiphyseal portion. The diaphyseal portion has an external periphery configured for placement in the medullary canal of the diaphysis of the long bone. The diaphyseal portion defines a longitudinally extending first surface of the diaphyseal portion. The first surface defines a longitudinally extending first void. The first epiphyseal portion extends from the diaphyseal portion. The first epiphyseal portion is configured for placement in the medullary canal of the first epiphysis of the long bone. The nail also includes a first insert positioned in the longitudinally extending first void of the diaphyseal portion. The first insert and the diaphyseal portion of the body are made from different materials.

According to an aspect of an embodiment of the disclosure, the first void of the diaphyseal portion of the body may include a slot, an aperture or a groove. According to yet another aspect of an embodiment of the disclosure, the diaphyseal portion of the body is made of a first material and the first insert is made of a second material. The first material has a modulus of elasticity greater than the modulus of elasticity of the second material.

According to another embodiment of the present disclosure there is provided an intramedullary nail for use in a medullary canal of a long bone. The nail defines a body having a length in a longitudinal direction and a width in the transverse direction normal to the longitudinal direction. The body defines a longitudinally extending first void that does not penetrate the body in the transverse direction.

According to yet another embodiment of the present disclosure there is provided an intramedullary nail for use in a medullary canal of a long bone. The intramedullary nail includes a nail having a length in a longitudinal direction and a width in a transverse direction normal to the longitudinal direction. The nail is made of a first material and defines a longitudinally extending first void that does not penetrate the nail in the transverse direction. The intramedullary nail also includes a first insert made of a second material and configured for placement in the longitudinally extending void of the nail. The first material has a modulus of elasticity greater than the modulus of elasticity of the second material.

According to yet another embodiment of the present disclosure there is provided a method for performing trauma surgery on a long bone. The method includes the step of providing an intramedullary nail. The nail includes a body having a diaphyseal portion and an epiphyseal portion. The diaphyseal portion has a diaphyseal portion length in a longitudinal direction and a diaphyseal portion width in a transverse direction normal to the longitudinal direction. The diaphyseal portion defines a longitudinally extending void of the diaphyseal portion of the nail. The method also includes the step of providing a first insert made of a second material. The first material has a modulus of elasticity greater than the modulus of elasticity of the second material. The method further includes the step of positioning the first insert in the longitudinally extending void of the diaphyseal portion of the nail. The method also includes the step of positioning the nail in the medullary canal.

Technical advantages of the present invention will be readily apparent to one skilled in the art from the following figures, descriptions and claims.

BRIEF DESCRIPTION OF THE DRAWINGS

Corresponding reference characters indicate corresponding parts throughout the several views. Like reference characters tend to indicate like parts throughout the several views.

DETAILED DESCRIPTION OF THE INVENTION

Embodiments of the present invention and the advantages thereof are best understood by referring to the following descriptions and drawings, wherein like numerals are used for like and corresponding parts of the drawings.

Figure 1:
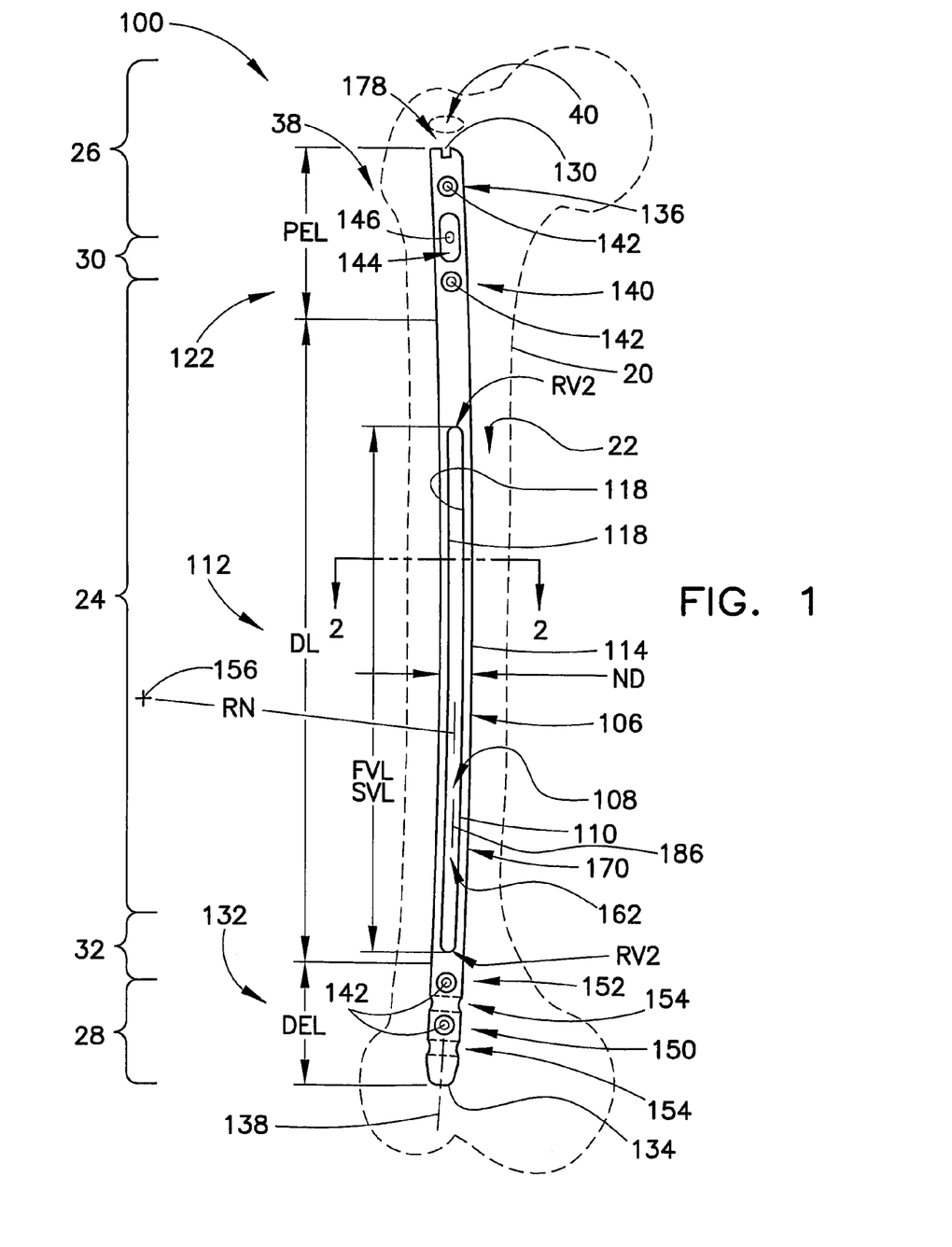
FIG. 1 is a medial/lateral view of an intramedullary nail in accordance with an embodiment of the present disclosure having a pair of opposed longitudinal grooves.

According to the present disclosure and referring now to FIG. 1, a composite flexible intramedullary nail 100 is shown. The nail 100 is adapted for use in the medullary canal 22 of a long bone, for example the femur 20. Such nails are also well suited for use in other long bones, for example the tibia and the humerus. The nail 100 includes a body 106 which defines a longitudinally extending first void 108. The nail 100 further includes a first insert 110 that is fitted in the first void 108 of the body 106. The first insert 110 is made of a different material than the body 106. The first insert 110 is typically made of a more flexible material than the body 106 such that the nail 100 may be more easily advanced into the canal 22 of the femur 20 than a solid nail of the same shape. The added flexibility of the nail 100 permits the insertion of the nail 100 into the canal 22 of the femur 20 through the greater trochanter 38 or through the piriformis fossa 40 of the femur 20. The added flexibility of the intramedullary nail 100 also is helpful in reducing forces exerted by the nail 100 in the canal 22 on the femur 20 that may generate thigh pain.

While the body 106 may have any suitable shape, typically the body 106 has a shape that conforms to the medullary canal 22 of the femur 20. Since the shape of the medullary canal 22 is generally cylindrical and arcuate, the body 106 of the nail 100 typically has a generally cylindrical cross section and has an arcuate shape to match that of the canal 22.

The body 106 includes a central or diaphyseal portion 112. The diaphyseal portion 112 includes an external periphery 114 configured for placement in the medullary canal 22 of diaphysis 24 of the femur 20. The diaphyseal portion 112 defines the longitudinally extending first void 108. The diaphyseal portion 112 as shown in FIG. 1 is generally configured for placement in the diaphysis 24 of the femur 20.

The body 106 also includes a first or proximal epiphyseal portion 122 extending from the diaphyseal portion 112. The proximal epiphyseal portion 122 includes a proximal end 130 of the body 106 of the intramedullary nail 100. The proximal epiphyseal portion 122 is configured for placement in the medullary canal 22 of the proximal epiphysis 26 of the femur 20. Since the femur 20 includes a proximal metaphysis 30 positioned between the diaphysis 24 and the proximal epiphysis 26, a part of the diaphyseal portion 112 or a part of the proximal epiphyseal portion 122 of the body 106 of the nail 100, or both, passes through the proximal metaphysis 30 of the femur 20.

The proximal epiphyseal portion 122 may as shown have the same arcuate, cylindrical shape as the diaphyseal portion 112. Alternatively, the proximal epiphyseal portion may be straight and may have an irregular shape or a larger periphery than the diaphyseal portion of the nail. The proximal epiphyseal portion 122 of the nail 100 typically includes features for receiving fasteners to axially secure the nail 100 to the femur 20.

As shown in FIG. 1, the proximal epiphyseal portion 122 includes a first proximal opening 136 which extends transversely or perpendicular to longitudinal axis 138 of the nail 100. The nail 100 may further include additional transverse openings, for example second proximal opening 140. The second proximal opening 140 and the first proximal opening 136 may be adapted to receive first bone screws 142 (shown in phantom). The first bone screws 142 extend from first cortical exterior wall 44 of the femur 20 to opposed second cortical exterior wall 46 of the femur 20 (see FIG. 9). Such first bone screws 142 are typically cortical screws. It should be appreciated however that cancellous screws (not shown) may be used.

Referring again to FIG. 1, the proximal epiphyseal portion 122 further includes a proximal slot 144 for receiving second bone screw 146 that may be in the form of a cancellous screw. The second bone screw 146 may extend obliquely toward the greater trochanter 38 of the femur 20 or obliquely toward the neck 40 of the femur 20.

It should be appreciated that the intramedullary nail 100 may include only the diaphyseal portion 112 and the proximal epiphyseal portion 122. The intramedullary nail 100 may, however, as is shown in FIG. 1, further include a second or distal epiphyseal portion 132 extending from the diaphyseal portion 112 and opposed to the proximal epiphyseal portion 122. The distal epiphyseal portion 132 includes distal end 134 of the intramedullary nail 100. The distal epiphyseal portion 132 has the same arcuate, cylindrical shape as the diaphyseal portion 112 or, alternatively, may be straight and may have an irregular shape or a larger periphery than the diaphyseal portion 112 of the nail.

The distal epiphyseal portion 132 of the nail 100 is positioned in the distal epiphysis 28 of the femur 20. Since the distal metaphysis 32 of the femur 20 is positioned between the distal epiphysis 28 and the diaphysis 24, a part of the diaphyseal portion 112 or a part of the distal epiphyseal portion 132 of the body 106 of the nail 100, or both, passes through the distal metaphysis 32 of the femur 20.

The distal epiphyseal portion 132 typically includes features for securing the nail 100 to the femur 20 in the form of, for example, a first distal opening 150 extending transverse or normal to the longitudinal axis 138 of the nail 100. The distal epiphyseal portion 132 further includes a second distal opening 152 extending proximally from the first distal opening 150. The second distal opening 152 may similarly be transverse or normal to the longitudinal axis 138 of the nail 100. The first cortical screws 142 are fitted in the openings 150 and 152 and are secured to first cortical wall 44 and second cortical wall 46 of the femur 20. The distal epiphyseal portion 132 may further include additional openings 154 positioned normal to the first distal opening 150 and the second distal opening 152, as well as, normal to the longitudinal axis 138 of the nail 100. The first cortical screws 142 may similarly be fitted into the additional openings 154 in the distal epiphyseal portion 132 of the nail 100.

Figure 2:
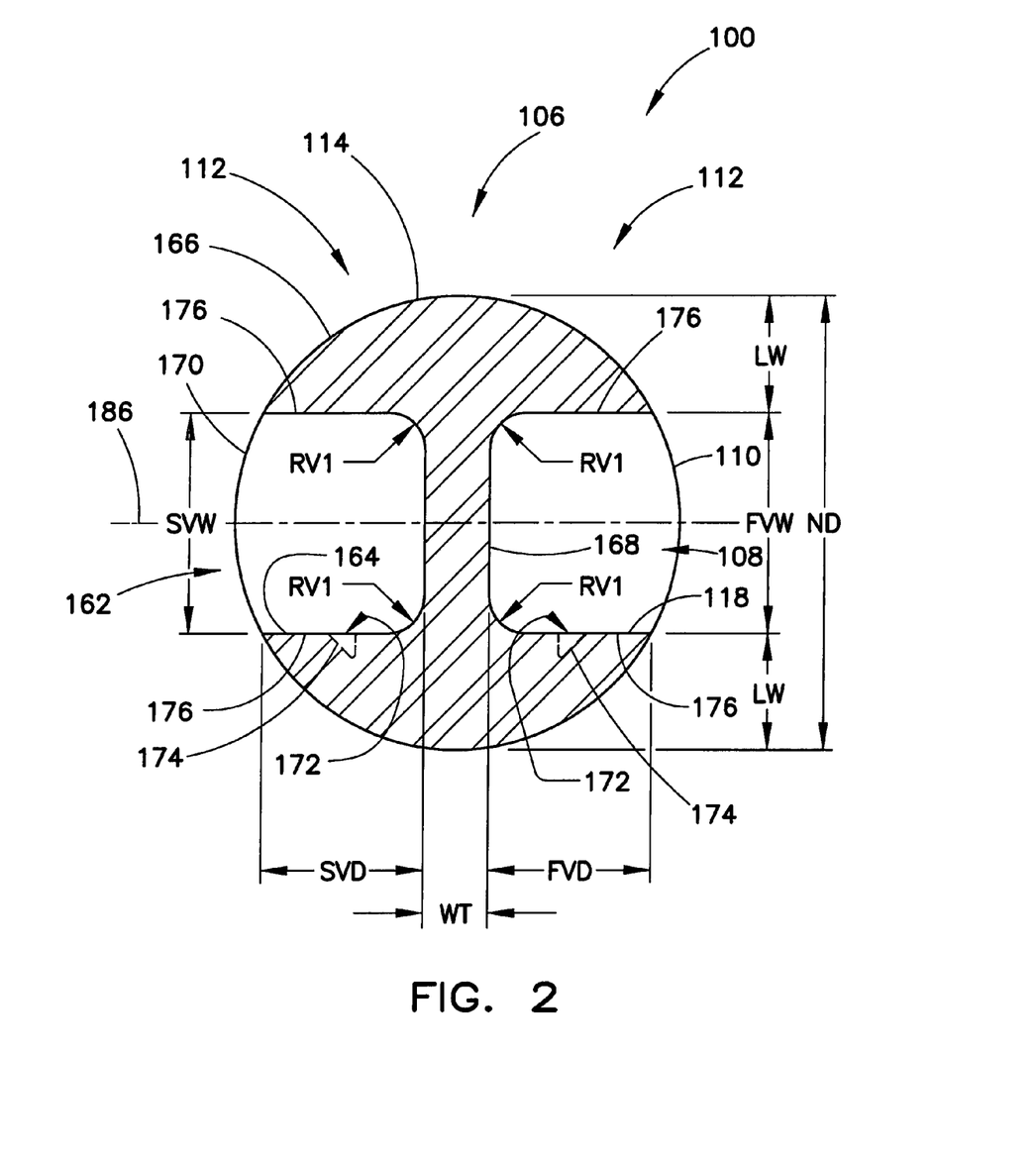
FIG. 2 is a cross section view of FIG. 1 along the line 2-2 in the direction of the arrows.

Referring now to FIGS. 1 and 2, the diaphyseal portion 112 of the body 106 of the nail 100 is shown in greater detail. The diaphyseal portion 112 has a generally circular cross section as shown in FIG. 2 and may be defined by, for example, external periphery 114 of the body 106 which may be defined by diameter ND. The cross section of the diaphyseal portion 112 alternatively may be a shape that is not circular, for example the cross section may be a polygon or an irregular shape. The cross section may be uniform in size, as shown, or may vary in size along the longitudinal axis 138.

The diaphyseal portion 112 is arcuate and is defined by a radius RN extending from origin 156, as shown in FIG. 1. The longitudinally extending first void 108 is defined by longitudinally extending first surface 118. The longitudinally extending first surface 118 may be arcuate with a radius of curvature. The first void 108 is defined by the spaced apart longitudinally extending first surfaces 118. The first void 108 may have a first void length FVL.

While the first void may have any suitable shape, as shown in FIG. 2, the first void 108 is in the form of a channel or groove formed in periphery 114 of the diaphyseal portion 112 of the body 106. The first void 108, for simplicity, has a generally rectangular cross section defined by first void width FVW and a first void depth FVD. The first void 108 does not penetrate the body 106 in a transverse direction normal to the longitudinal direction along the longitudinal axis 138 of nail 100.

While the nail of the present disclosure may be utilized with a solitary void or channel, it should be appreciated that a second void 162, as shown in FIG. 2, may be formed in the diaphyseal portion 112 of the body 106 of the nail 100. The second void 162 is formed from longitudinally extending second surface 164 of the diaphyseal portion 112. The second void 162 has a generally rectangular shape defined by second void depth SVD and a second void width SVW. The second void 162 does not penetrate the body 106 in a transverse direction normal to the longitudinal direction along the longitudinal axis 138 of nail 100. First void radii RV1 and second void radii RV2 may be formed in the first void 108 and in the second void 162 to minimize stress risers. The first void 108 and the second void 162 define opposed lands 166 and a web portion 168. It should be appreciated that by altering the depth of the first void 108 and the second void 162, the central web 168 may vary, increasing or decreasing the web thickness WT. Similarly, the lands 166 may have a land width LW that may be increased or decreased to adjust the flexibility of the body 106 of the nail 100.

The voids 108 and 162 may be positioned anywhere around the periphery of the body 106 of the nail 100. To provide additional flexibility in the anterior posterior plane to permit the nail to match the arcuate shape of the canal 22 of the femur 20 in the anterior posterior plane, the voids 108 and 162 are oriented relative to medial/lateral plane 186.

Referring again to FIG. 1, the second void 162 may have a second void length SVL. The first void length FVL and the second void length SVL are considerably longer than diameter ND of the body 106 of the nail 100. For example the void length FVL and the second void length SVL may be at least five times longer, at least ten times longer, or at least fifteen times longer than diameter ND. The first void 108 and the second void 162 are spaced from the first end 130 and the second end 134 of the body 106 of nail 100. For example, the first void 108 and the second void 162 may be spaced a distance of at least 50 millimeters from the first end 130 and the second end 134 of the body 106 of nail 100. For example, the first void 108 and the second void 162 may be spaced a distance of at least 75 millimeters from the first end 130 and the second end 134 of the body 106 of nail 100.

The diaphyseal portion 112 of the body 106 of the nail 100 has a length DL that is greater than length PEL of the proximal epiphyseal portion 122 of the body 106 of the nail 100 or length DEL of the distal epiphyseal portion 132 of the body 106 of the nail 100. For example length DL of the diaphyseal portion 112 may be at least twice as great as the length PEL of the proximal epiphyseal portion 122 or the length DEL of the distal epiphyseal portion 132. For example length DL of the diaphyseal portion 112 may be at least three times as great as the length PEL of the proximal epiphyseal portion 122 or the length DEL of the distal epiphyseal portion 132.

The body 106 of the nail 100, as shown, is integral with the diaphyseal portion 112 and the epiphyseal portions 122 and 132 being made of the same material. The diaphyseal portion 112 may be made of any suitable durable material and may for example be made of a metal. The diaphyseal portion 112 should be a material compatible with the human anatomy. The diaphyseal portion 112, if made of a metal, may be made of, for example, a cobalt chromium alloy, a stainless steel alloy, or a titanium alloy.

With continued reference to FIGS. 1 and 2, the nail 100 of the present disclosure further includes first insert 110. The first insert 110 is fitted into the first void 108. Similarly, the nail 100 includes a second insert 170 which is fitted into the second void 162. It should be appreciated that the first insert 110 has a size and shape to match that of the first void 108 and the second insert 170 has a size and shape to match that of second void 162. For simplicity, the first void 108 may have a size and shape nominally the same as the second void and the first insert 110 may correspondingly have a size and shape nominally the same as the second insert 170.

The inserts 110 and 170 may be fitted into the voids 108 and 162, respectively, in any suitable manner. For example and as shown in FIG. 2, the diaphyseal portion 112 of the body 106 of the nail 100 may include opposed cavities 172 that mate with protrusions 174 formed on the first insert 110 and on the second insert 170. Alternatively, opposed walls 176 of the first insert 110 and 170 may be in interference fit or taper lock fit with the mating walls of the voids 108 and 162 such that the inserts 110 and 170 are secure in the voids 108 and 162, respectively.

Alternatively, the first insert 110 and the second insert 170 may be secured to the voids 108 and 162 by an adhesive, for example, glue. Alternatively, it should be appreciated that fasteners such as screws (not shown) may be utilized to secure the inserts 110 and 170 into voids 108 and 162 of the diaphyseal portion 112 of the body 106 of the nail 100.

Alternatively, it should be appreciated that the first insert 110 and the second insert 170 may flow into the voids 108 and 162, respectively, of the nail 110 in a liquid or molten state. Features may be provided in the surfaces of body 106 to secure the inserts 110 and 170 after the liquid material solidifies. The first insert 110 and the second insert 170 may be molded into the first void 108 and the second void 162 in any suitable fashion. For example, the first insert 110 and the second insert 170 may be molded onto the nail 110 as a procedure during the manufacturing of the nail 110 or may be placed onto the nail 110 in the operating room based upon patient's specific information.

The nail 100 may as shown in FIG. 1 include a longitudinal or axial opening 178 extending from proximal end 130 of the nail 100 to the first void 108 and the second void 162. The placement of a longitudinal opening 178 may permit a liquid material, for example a polymer, to be placed intraoperatively through the longitudinal opening 178 and into the first void 108 and the second void 162 of the nail 100.

The first insert 110 and the second insert 170 may be made of any suitable durable material compatible with the human anatomy and is typically made of a material having a rigidity which is less than the rigidity of the material of which the diaphyseal portion 112 of the body 106 of the nail 100 is made.

While many measurements of rigidity may be made. For simplicity for the materials utilized in this device the measurement of Modulus of Elasticity may be used. The Definition of Modulus of Elasticity is the ratio of stress (nominal) to corresponding strain below the proportional limit of a material. It is expressed in force per unit area, usually pounds per square inch or kilograms-force per square centimeter. For example, the first insert 110 and the second insert 170 may be made of a material having a modulus of elasticity which is less than the modulus elasticity of the diaphyseal portion 112. For example, the first insert 110 and the second insert 170 may be made of a polymer, for example polyethylene, for example ultra high molecular weight polyethylene, for example MARATHON® Cross-linked Polyethylene, sold by DePuy Orthopaedics, Inc., Warsaw, Ind.

As shown in FIG. 2, the rigidity of the nail 100 is a combination of the rigidity of the body 106, as well as of the rigidity of the first insert 110 and the second insert 170. It should be appreciated that if the rigidity of the material from which the first insert 110 and the second insert 170 is made is less than the rigidity of the body 106 of the nail 100, the rigidity of the nail 100 is less than it would be were the body 106 to have a solid cylindrical cross section. Further it should be appreciated that the smaller the web thickness WT of the web 168 and the land width LW of the lands 166, the more flexible the nail 100. It should further be appreciated that the less rigid the materials for which the body 106 and the inserts 110 and 170 are made, the less rigid the nail 100.

It should be appreciated that the first void 108 and the second void 162 should be sized such that the lands 166 and the web 168, in combination with the selection of the materials for the body 106 and the inserts 110 and 170, provide the nail 100 with the desired rigidity so that the nail 100 may be easily inserted through either the piriformis fossa or the greater trochanter.

When utilizing the composite flexible intramedullary nail of the present disclosure it may be desirable to provide rigidity to the nail that mimics or replicates the rigidity of the patient's bone. Thus, specific patient information, such as age, weight, and activity, as well as patient's specific bone geometry, may be utilized to obtain the desired rigidity of the nail 100. For example, X-Ray films or CAT scans may be taken of the patient's bone to ascertain the size of the bone and the thicknesses of the cortical walls to determine the rigidity of the patient's bone. Based on this information, the materials and shape of the nail 100 and the inserts 110 and 170 may be determined to obtain a nail with a rigidity matching that of the patient's bone.

Figure 3:
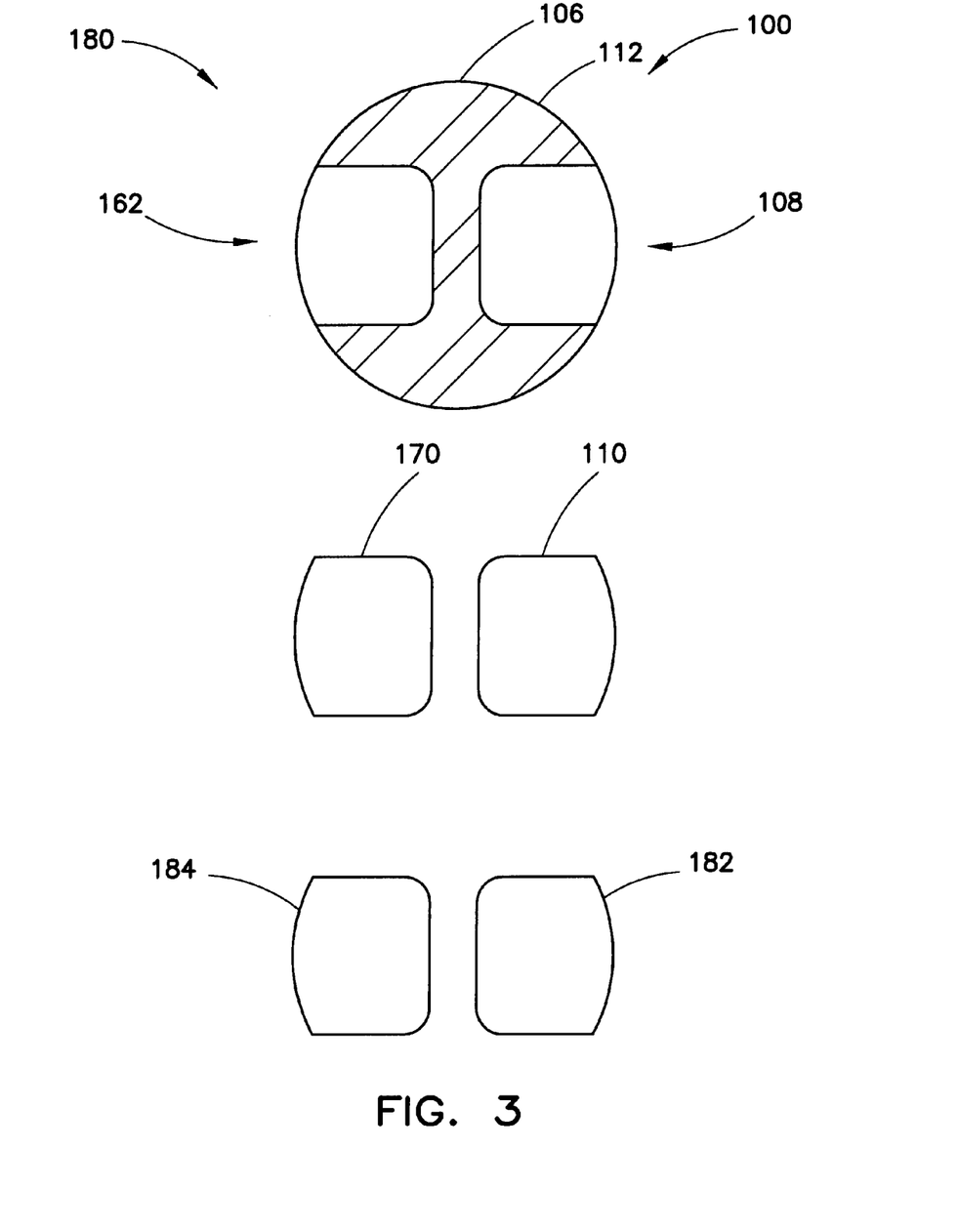
FIG. 3 is a schematic view of an intramedullary nail kit according to yet another embodiment of the present disclosure.

To provide matching nails for a wide variety of patients, a kit 180 as shown in FIG. 3 may be utilized in accordance with another embodiment of the disclosure. The kit 180 includes a variety of sets of replaceable inserts, with each set having a different rigidity. A variety of nails may be constructed with an identical body and with one of the sets of inserts to provide a nail that has a rigidity to match that of the bone of the patient. The kit 180 includes the body 106 as well as a first set of inserts in the form of first insert 110 and second insert 170, both made of a first material with a first rigidity, configured to matingly fit in the first void 108 and the second void 162, respectively. The kit 180 may further include a second set of inserts, both made of a second material with a second rigidity, in the in the form of third insert 182 having a shape similar to that of first insert 110 and a fourth insert 184 with a shape similar to that of second insert 170. The third insert 182 and the fourth insert 184 may have a rigidity of, for example, less or greater than the rigidity of the first insert 110 and the second insert 170. The third insert 182 and the fourth insert 184, may include cavities or voids such that the rigidity of the third insert 182 and the fourth insert 184 is less than the rigidity of the first and second inserts 110 and 170, yet made of the same material. The kit 180 of FIG. 3 may further include a third set of inserts, for example, fifth insert (not shown), and sixth insert (not shown), made of yet a third material with yet a third rigidity, as well as a fourth set of inserts, for example, a seventh and eighth insert (not shown), made of yet a fourth material with yet a fourth rigidity, and so forth. The kit of 180 may be utilized to provide a surgical procedure such that a custom rigidity nail may be implanted in the patient utilizing a common body and a selected one set of several sets of inserts.

Figure 4:
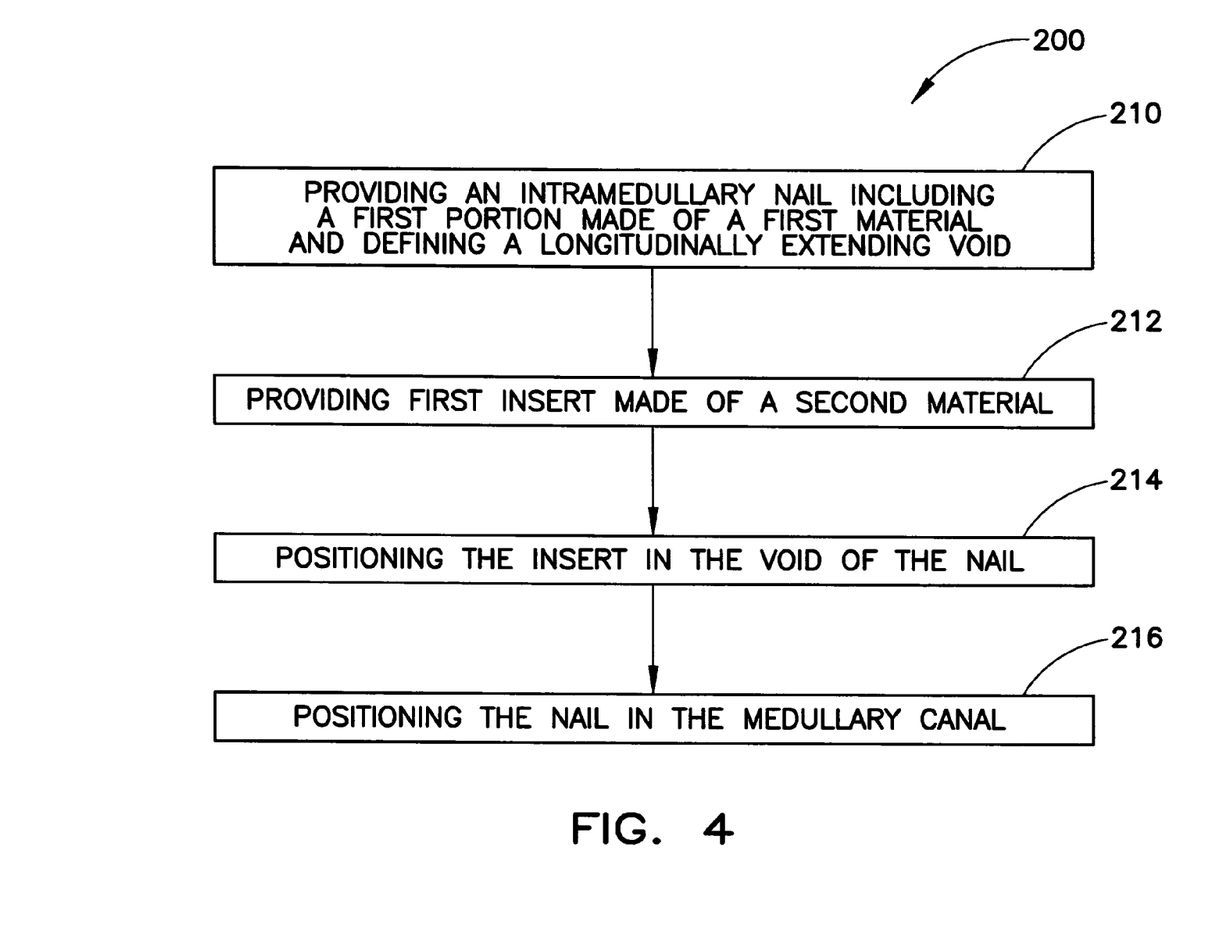
FIG. 4 is a flow diagram of a method of performing trauma surgery in accordance with another embodiment of the present disclosure.

According to the present disclosure and referring now to FIG. 4, a method 200 of performing trauma surgery on a long bone is shown as method or surgical procedure 200. The method 200 may utilize the kit 180 of FIG. 3 and the method 200 includes a step 210 of providing an intramedullary nail.

The nail includes a body having a diaphyseal portion and an epiphyseal portion. The diaphyseal portion has a diaphyseal portion length in the longitudinal direction and a diaphyseal portion width in the transverse direction normal to the longitudinal direction. The diaphyseal portion defines a longitudinally extending void of the diaphyseal portion. The void has a void length in the longitudinal direction. The void length may be greater than the diaphysis portion width. For example the void length may be least five, ten, or fifteen times greater than the diaphyseal portion width. The diaphyseal portion is made of a first material.

The method 200 further includes a step 212 of providing a first insert. The first insert is made of a second material and is positionable in the longitudinally extending void of the diaphyseal portion of the nail. The first material has a modulus of elasticity greater than the modulus of elasticity of the second material. The method 200 further includes a step 214 of positioning the insert in the void of the nail. The method 200 further includes a step 216 of positioning the nail in the medullary canal.

The method 200 may further include a step of providing a second insert made of a third material and configured for removable placement in the longitudinally extending void of the diaphyseal portion of the nail. The third material has a modulus of elasticity different from the modulus elasticity of the second material. The step of positioning the insert in the void of the nail 214 includes the steps of selecting one of the first insert and the second insert based on patient's specific information and positioning the selected one of the first insert and the second insert in the void of the nail. Thus, the surgeon may intraoperatively or preoperatively examine the patient and make measurements, observations, performs tests, and take data of the patient. The information obtained may include the patient's activity level, age, general health, weight and the specific characteristics of the patient's bone into which the nail is to be placed. The specific characteristics may include the overall size of the bone, the thickness of the cortical wall, and the density of the cancellous portion of the bone. The surgeon may then select the first insert or the second insert in order to build a nail that matches the rigidity of the patient's bone. The inserts, when used with the nail kit 180 of FIG. 3, may be used as matched pairs, such as inserts 110 and 170 or inserts 182 and 184. It should be appreciated that the third, fourth and other additional inserts may be included in the nail kit that the surgeon brings to the operating room.

The method 200 may further include a step of preparing a cavity in the medullary canal of the diaphysis of a long bone through a selected one of the piriformis fossa or the greater trochanter of the first epiphysis of the long bone. The surgeon may make his selection based upon the condition of the bone and/or his preference. The surgeon may utilize the intramedullary nail of the present disclosure and selectively prepare the cavity through the piriformis fossa or the greater trochanter and utilize the same nail. This is possible because of the added flexibility of the flexible composite nail of the disclosure. The step of positioning the nail in the medullary canal may include the step of inserting the nail through the selected one of the piriformis fossa or the greater trochanter.

Figure 5:
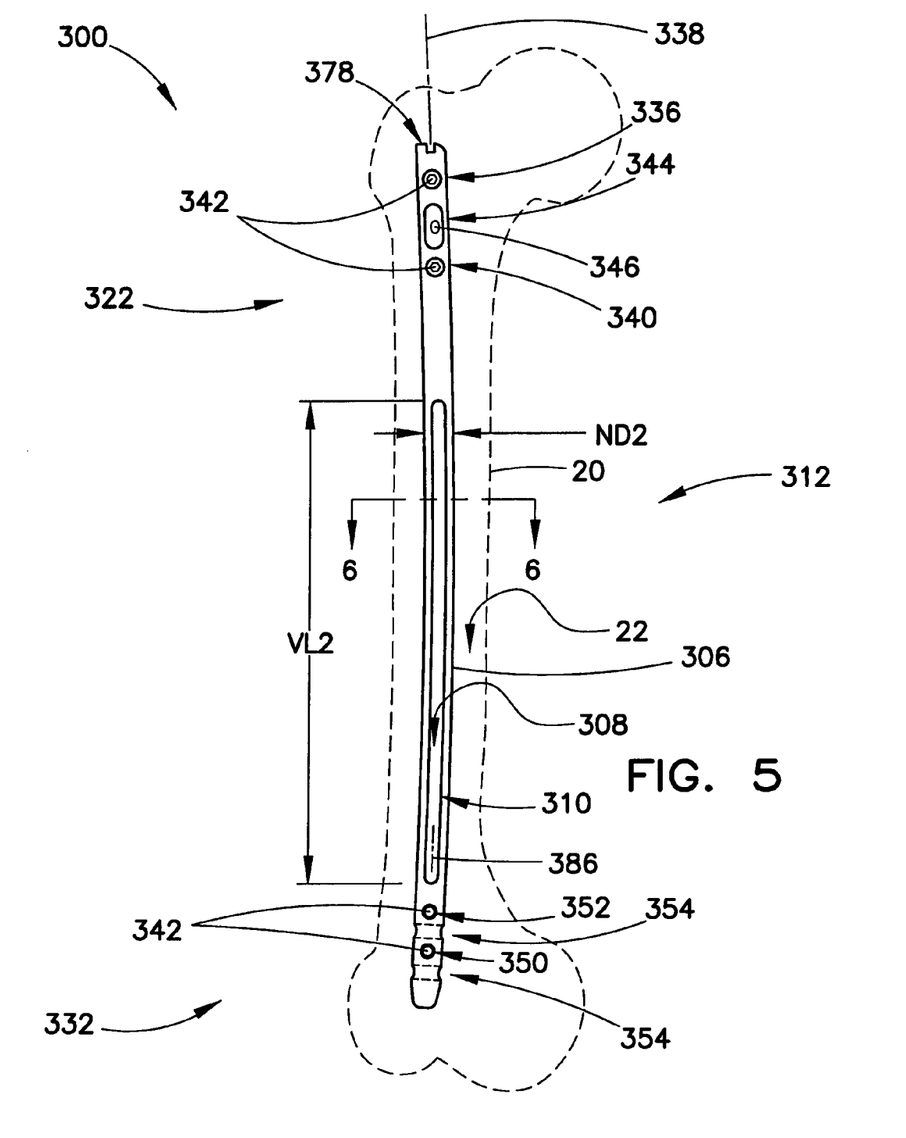
FIG. 5 is a medial/lateral view of an intramedullary nail in accordance with another embodiment of the present disclosure having a longitudinal slot.
Figure 6:
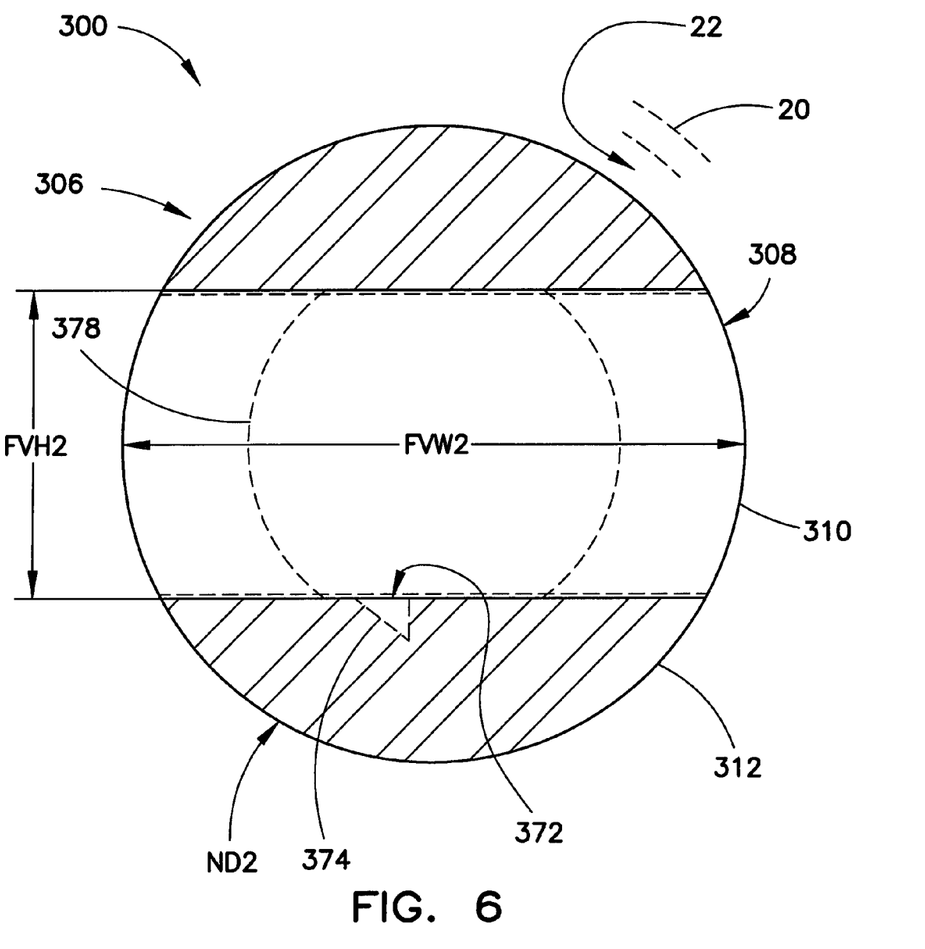
FIG. 6 is a cross section view of FIG. 5 along the line 6-6 in the direction of the arrows.

While it should be appreciated that the nail of the present disclosure may include the pair of spaced apart voids or channels as shown in FIGS. 1 and 2, alternative shapes and configurations of voids may be used. For example, the voids of the nail of the present disclosure may be in the form of a slot or a longitudinal opening. For example and as shown in FIGS. 5 and 6, another embodiment of the present disclosure is shown as intramedullary nail 300. The nail 300 includes a body 306 having a diaphyseal portion 312 as well as a first or proximal epiphyseal portion 322 extending from the diaphyseal portion 312 and a second or distal epiphyseal portion 332 positioned opposed to the proximal epiphyseal portion 322. The diaphyseal portion 312 includes a void 308. The void 308 is in the form of a longitudinally extending slot. The slot 308 may, as shown in FIGS. 5 and 6, be centrally located or alternatively, may be biased from center line 338 of the nail 300. The slot 308 may be positioned such that the groove center line is in plane 386 co-planar with the medial/lateral plane of the femur to permit additional flexibility of the nail 300 to conform to the arcuate shape of canal 22 of the femur 20.

The void 308 may have any suitable shape and, as shown in FIG. 6 for simplicity, has a generally rectangular cross section defined by a void height FVH2 and a void width FVW2. The void width FVW2 may be the same as diameter ND2 of the body 306 of the nail 300 such that when an insert is installed, the periphery 314 of the nail 300 remains uniform throughout its periphery. As shown in FIG. 5, the void 308 may be arcuate with a radius of curvature. The void 308 may have a void length VL2. The void length VL2 is considerably longer than diameter ND2 of the body 306 of the nail 300. For example the void length VL2 may be at least five times longer, at least ten times longer, or at least fifteen times longer than diameter ND2. The first void 308 is spaced from the first end 330 and the second end 334 of the body 306 of nail 300. For example, the first void 308 may be spaced a distance of at least 50 millimeters from the first end 330 and the second end 334 of the body 306 of nail 300. For example, the first void 308 may be spaced a distance of at least 75 millimeters from the first end 330 and the second end 334 of the body 306 of nail 300.

The body 306 includes the diaphyseal portion 312 as well as the proximal epiphyseal portion 322 and the distal epiphyseal portion 332 and is shown with a unitary construction. Alternatively, the body 306 may be modular. The proximal epiphyseal portion 322 includes a first proximal opening 336 and a second proximal opening 340 spaced from the first proximal opening 336. The proximal openings 336 and 340 each receive a cortical bone screw 342 as shown in phantom. The proximal epiphyseal portion 322 further includes a proximal slot 344 for receiving a cancellous bone screw 346 as shown in phantom.

The distal epiphyseal portion 332 may include a first distal opening 350 and a spaced apart second distal opening 352. The distal openings 350 and 352 may be adapted to receiving the cortical bone screws 342. The distal epiphyseal portion 332 may further include additional transverse distal openings 354 spaced from the first distal opening 350 and the second distal opening 352. The additional distal openings 354 may be adapted for receiving the cortical screws 342.

Nail 300 further includes a first insert 310 that matingly fits in the longitudinally extending void 308. The first insert 310 has a size and shape that matingly fits in the void 308. The first insert 310 may be secured in the void 308 in any suitable fashion. For example, the first insert 310 may be interferencely fitted into the void 308 or the void 308 may be placed in a fluid or liquid state into the void 308 and secured by solidifying in the void 308. The diaphyseal portion 312 of the body 306 of the nail 300 may include a feature in the form of a notch 372 into which a protrusion 374 formed on the first insert 310 matingly fits.

The first insert 310 may be placed into the void 308 of the body 306 of the nail 300 preoperatively or intraoperatively. For example, the nail 300 may be provided with insert in tact upon receipt at the hospital. Alternatively, a variety of inserts each having different rigidities may be available for the surgeon to place in the body 306 of nail 300 in the operating room upon selection by the surgeon of the proper insert. Alternatively, the first insert 310 may be positioned intraoperatively. If inserted intraoperatively, the first insert 310 may be positioned in the void 308 by inserting the insert 310 in a liquid form through longitudinal opening 378 in the body 306 of the nail 300.

Figure 7:
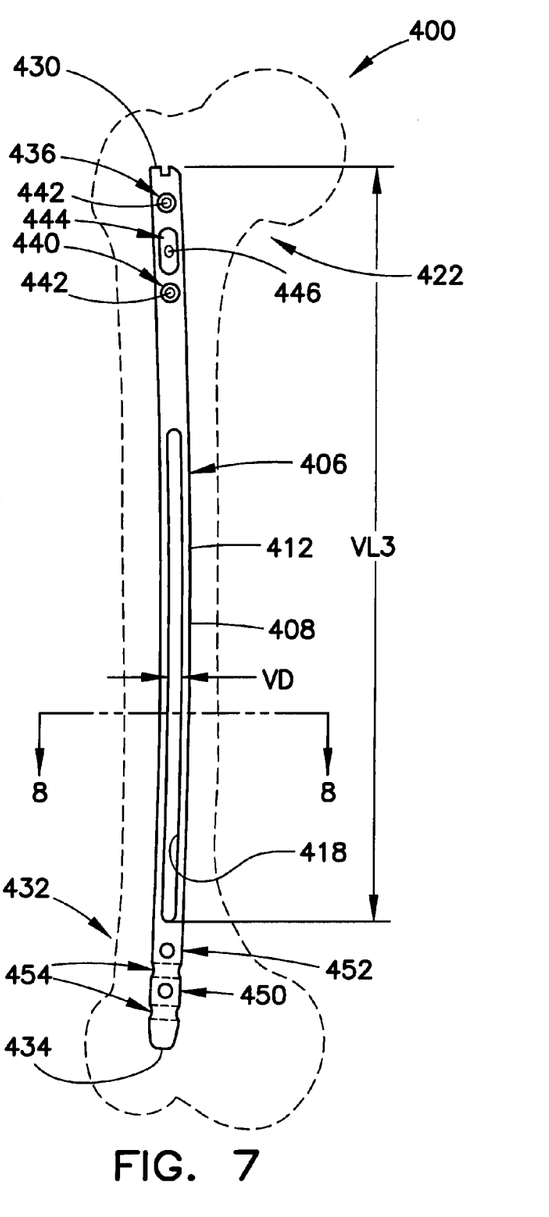
FIG. 7 is a medial/lateral view of an intramedullary nail in accordance with yet another embodiment of the present disclosure having a longitudinal aperture.
Figure 8:
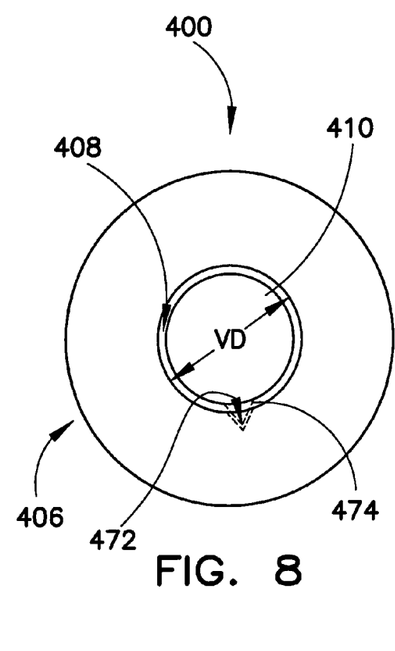
FIG. 8 is a cross section view of FIG. 7 along the line 8-8 in the direction of the arrows.

Referring now to FIGS. 7 and 8 yet another embodiment of the present disclosure is shown as intramedullary nail 400. Intramedullary nail 400 is similar to the intramedullary nail 300 of FIGS. 5 and 6 except that the intramedullary nail 400 has a void 408 in the form of a longitudinal opening or cannula formed in the body of the nail 400. The nail 400 includes a body 406 having a generally cylindrical shape and including a diaphyseal portion 412. The nail 400 also includes a first or proximal epiphyseal portion 422 extending from the diaphyseal portion 412 to proximal end 430 of the nail 400 and a second or distal epiphyseal portion 432 extending from the diaphyseal portion 312 to distal end 434 of the nail 400. The diaphyseal portion 412 includes a first surface 418 forming a longitudinal aperture, an internal void or cannula 408. The void 408 extends a void length VL3 from the proximal end 430 of the body 406 of the nail 400.

The nail 400 further includes an insert 410 which is fitted in the void 408. The insert 410 has a generally circular cross section and is matingly fitted to fill the void 408 defined by void diameter VD. The insert 410 is inserted at proximal end 430 of the nail 400 into void 408. It should be appreciated that the insert 410 may be inserted in the nail through the proximal end 430 during manufacture, in the operating room, or intraoperatively, with the body 406 of the nail 400 inserted into the femur 20 of the patient prior to placing the insert 410 into the body 406. The insert 410 may be positioned or placed in a solid condition through the void 408 or may be placed as a liquid into the void 408. It should be appreciated that the insert 410 may be secured to the body 406 by a protrusion 474 that fits into a notch 472 formed in the diaphyseal portion 410 of the body 406 of the nail 400, by an interference fit, by fasteners, or by glue.

The proximal epiphyseal portion 422 of the body 406 of the nail 400 may further include proximal openings 436 and 440 for receiving cortical screws 442, as well as a proximal slot 444 for receiving a cancellous bone screw 446. The distal epiphyseal portion 432 of the body 406 of the nail 400 may include distal openings 450, 452 and 454 for receiving the cortical bone screws 442.

It should be appreciated that the void of the present disclosure may include void portions of various shapes or configurations. For example the void may include a slot portion, a groove portion and an aperture portion, or any combination of these portions. Alternatively a nail may include separate voids of various types including a slot, a groove and an aperture or any combination of these voids. Such nails may include insert that conform to the shapes of the respective slots, grooves and apertures or portion of slots, grooves and apertures.

Of course, numerous other adaptations are possible. Moreover, there are advantages to individual advancements described herein that may be obtained without incorporating other aspects described above. Therefore, the spirit and scope of the appended claims should not be limited to the description of the preferred embodiments contained herein.

What is claimed is:

1. An intramedullary nail for use in a medullary canal of an epiphysis and a diaphysis of a long bone, said nail comprising:
    a body having a length in a longitudinal direction and a width in a transverse direction normal to the longitudinal direction, said body including a diaphyseal portion including an external periphery configured for placement in the medullary canal of the diaphysis of the long bone, the diaphyseal portion defining a longitudinally extending first surface thereof, the first surface defining a longitudinally extending first void and a proximal epiphyseal portion extending from the diaphyseal portion, the proximal epiphyseal portion configured for placement in the medullary canal of the first epiphysis of the long bone, and said first void being spaced apart from said proximal epiphyseal portion; and
    a first insert positioned in the longitudinally extending first void of the diaphyseal portion, the first insert and the diaphyseal portion of said body being made from different materials,
    wherein said first void possesses a first size and shape along a longitudinal extent of said first void,
    wherein said first insert possesses a second size and shape, and
    wherein said first size and shape matches said second size and shape along the longitudinal extent and a cross-section of said first void so that said first insert is fitted in said first void and is contained within said exterior periphery when said body is within the medullary canal, wherein when said first insert is installed, said external periphery remains uniform throughout said external periphery when viewed in a cross sectional plane normal to the longitudinal direction.

2. The nail as in claim 1:
    wherein the diaphyseal portion of said body further defines a longitudinally extending second surface thereof opposed to the first surface, the longitudinally extending second surface defining a second void; and
    further comprising a second insert positioned in the second void of the diaphyseal portion of said body.

3. The nail as in claim 1, wherein the first void of the diaphyseal portion of said body comprises at least one of a slot, a groove and an aperture.

4. The nail as in claim 2, wherein each of the first void and second void of the diaphyseal portion of said body comprises a slot, a groove and an aperture.

5. The nail as in claim 1, wherein the first void of the diaphyseal portion of said body does not penetrate said body in the transverse direction.

6. The nail as in claim 1, wherein the diaphyseal portion of said body and said proximal epiphyseal portion of said body are integral with each other.

7. The nail as in claim 1, wherein the material of said first insert has a modulus of elasticity greater than the modulus of elasticity of the material of said body.

8. The nail of claim 7, wherein the modulus of elasticity of said insert and the size of the first void of the diaphyseal portion of said body are selected to permit the nail to bend to conform to the medullary canal.

9. The nail as in claim 1, wherein the first void of the diaphyseal portion of said body has a length at least ten times the width of said body.

10. The nail as in claim 1:
    wherein the diaphyseal portion of said body comprises a metal; and
    wherein said first insert comprises a biocompatible material.

11. The nail of claim 10, wherein said first insert comprises a polymer.

12. The nail as in claim 1, wherein said body further includes a distal epiphyseal portion extending from the diaphyseal portion of said body and opposed to the proximal epiphyseal portion of said body, the distal epiphyseal portion of said body configured for placement in the medullary canal of a second epiphysis of the long bone.

13. The nail as in claim 1:
wherein said body has a first end and a second end opposed to the first end in the longitudinal direction; and
wherein the first void of said body is spaced from the first end of said body and spaced from the second end of said body.

14. An intramedullary nail for use in a medullary canal of a long bone, said nail comprising:
a nail body having a length in a longitudinal direction and a width in a transverse direction normal to the longitudinal direction, said nail body made of a first material and defining a longitudinally extending first void; and
a first insert made of a second material and configured for placement in the longitudinally extending first void of said nail body, the first material having a modulus of elasticity greater than the modulus of elasticity of the second material, said first insert engaged within said first void so that the rigidity of the intramedullary nail is a combination of the modulus of elasticity of said first and second materials,
wherein said first void possesses a first size and shape,
wherein said first insert possesses a second size and shape, and
wherein said first size and shape matches said second size and shape such that said first insert is fitted in said first void, wherein said nail body defines an external periphery thereof, such that when said first insert is installed, said external periphery remains uniform throughout said external periphery when viewed in a cross sectional plane normal to the longitudinal direction.

15. The nail of claim 14, wherein the modulus of elasticity of the second material and the size of the void of said body are selected to permit the nail to bend to conform to the medullary canal.

16. The nail as in claim 14, wherein the longitudinally extending first void of said nail body comprises a groove.

17. The nail as in claim 16, said nail body further defining a wall extending inwardly from the external periphery and a bottom surface extending from the wall and opposed to the external periphery of said nail body, the wall and the bottom surface defining the groove.

18. The nail as in claim 14, wherein the first void of said nail body has a length at least ten times the width of said nail body.

19. The nail as in claim 14, wherein said nail body further defines a longitudinally extending second void, the second void spaced from the first void.

20. The nail as in claim 14:
wherein the first material comprises a metal; and
wherein said first insert comprises a biocompatible material.

21. The nail of claim 20, wherein said first insert comprises a polymer.

22. The nail as in claim 14, wherein said first insert is removeably positionable in the void of said nail body.

23. The nail as in claim 14, further comprising a second insert made of a third material and configured for removable placement in the longitudinally extending first void of said nail body, the third material having a modulus of elasticity different than the modulus of elasticity of the second material.

* * * * *